United States Patent [19]
McDonald

[11] Patent Number: 5,919,197
[45] Date of Patent: Jul. 6, 1999

[54] INSERTION OF MULTIPLE FOLDED LENS INTO THE EYE

[75] Inventor: Henry H. McDonald, Rancho Mirage, Calif.

[73] Assignee: Surgical Concepts, Inc., Newport Beach, Calif.

[21] Appl. No.: 08/841,768

[22] Filed: May 5, 1997

[51] Int. Cl.$^6$ .................................................. A61F 9/00
[52] U.S. Cl. ................................................ 606/107; 623/6
[58] Field of Search ........................ 606/1, 107; 673/4, 673/6

[56] References Cited

U.S. PATENT DOCUMENTS

| | | |
|---|---|---|
| 4,813,957 | 3/1989 | McDonald . |
| 4,959,070 | 9/1990 | McDonald . |
| 5,190,552 | 3/1993 | Kelman ..................................... 606/107 |
| 5,203,790 | 4/1993 | McDonald . |
| 5,217,464 | 6/1993 | Mcdonald . |
| 5,549,614 | 8/1996 | Tunis ........................................ 606/107 |
| 5,562,676 | 10/1996 | Brady et al. ............................ 606/107 |
| 5,578,042 | 11/1996 | Cumming ................................ 606/107 |
| 5,578,080 | 11/1996 | McDonald . |
| 5,702,402 | 12/1997 | Brady ....................................... 606/107 |
| 5,711,317 | 1/1998 | Mcdonald ................................ 606/107 |

*Primary Examiner*—Glenn K. Dawson
*Attorney, Agent, or Firm*—William W. Haefliger

[57] ABSTRACT

The method of implanting an artificial lens in the eye that includes providing the lens to have folded M configuration, with two laterally spaced legs interconnected by a U-shaped portion; providing an elongated insertion tube having a distal end insertible into the eye; traveling the M-folded lens in the tube toward the distal end preparatory to insertion into the eye.

9 Claims, 5 Drawing Sheets

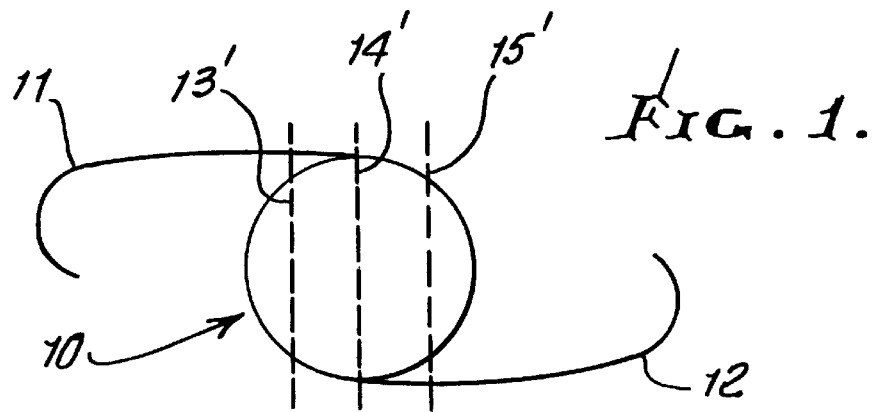
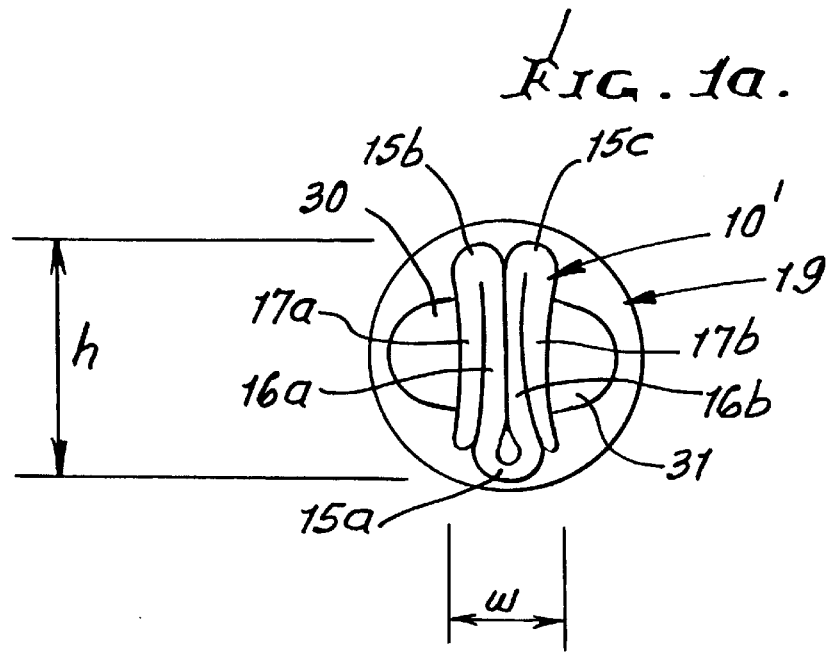
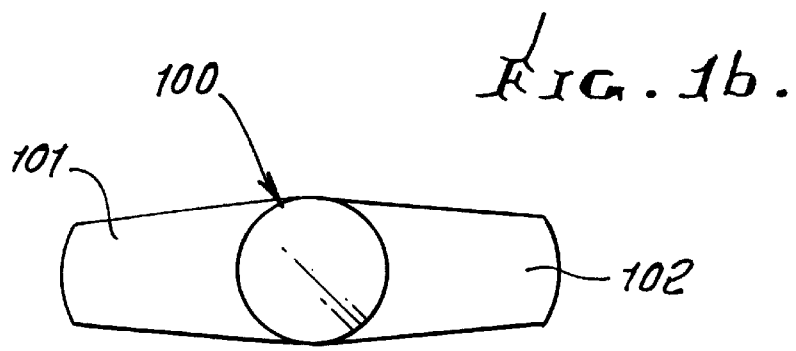

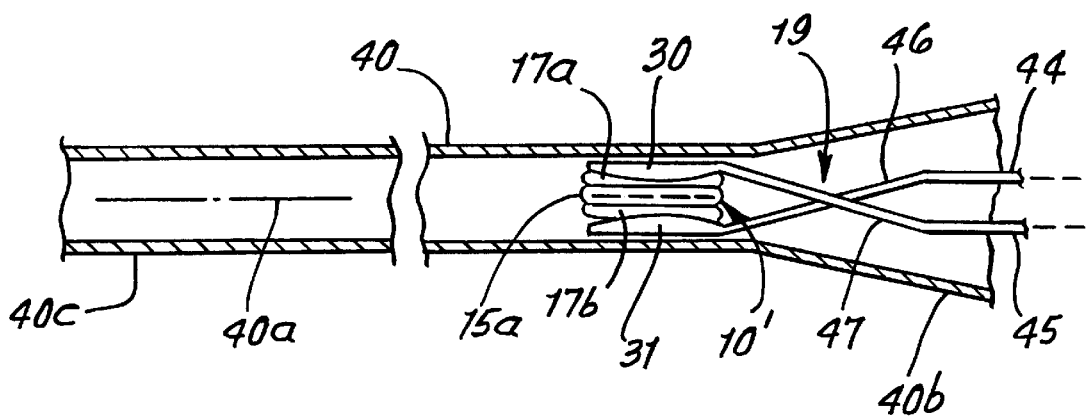
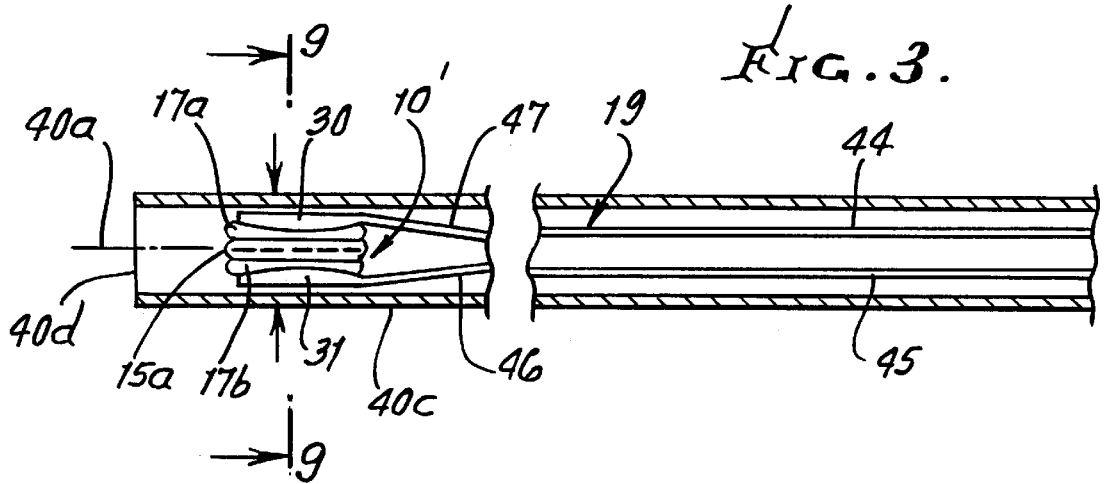
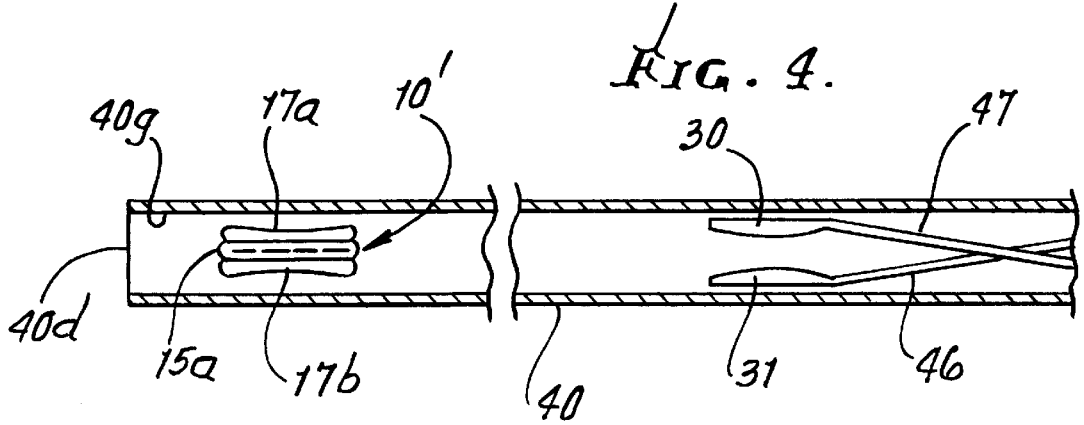

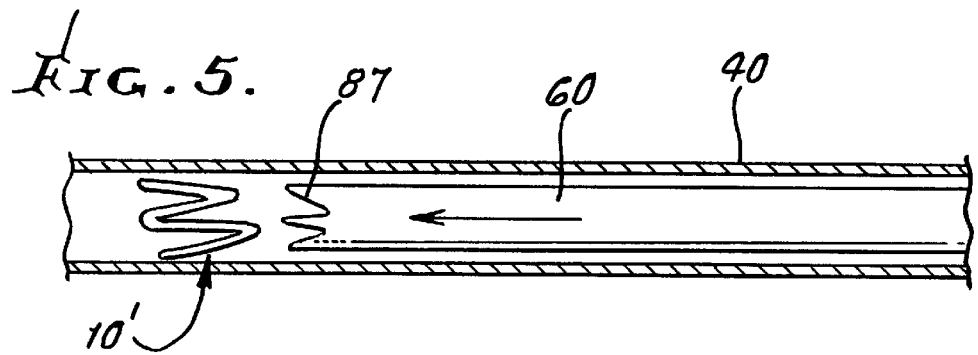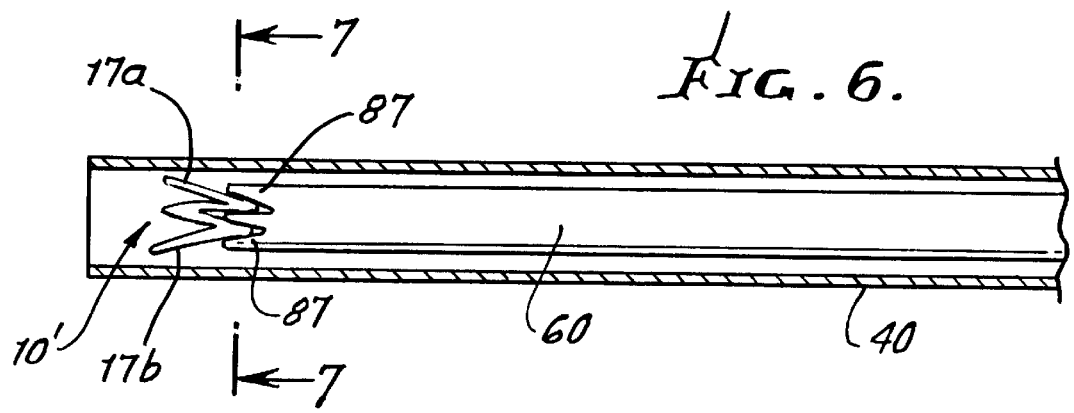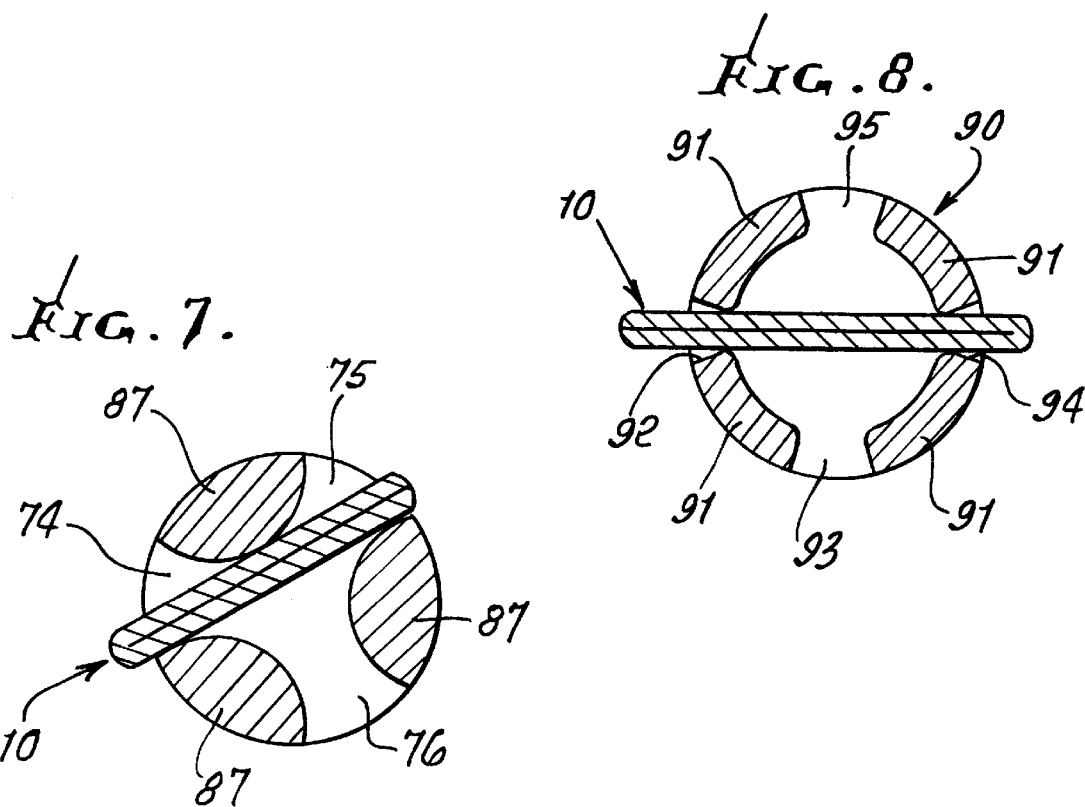

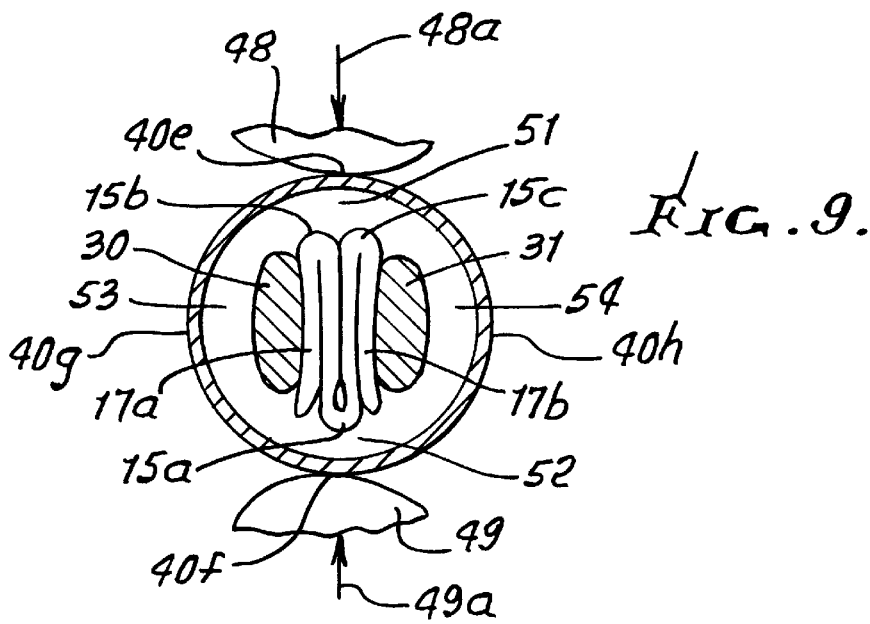
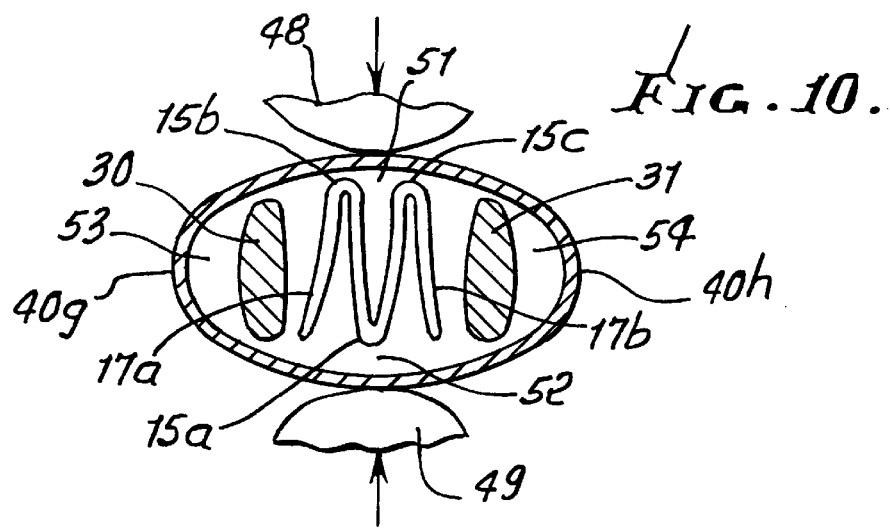
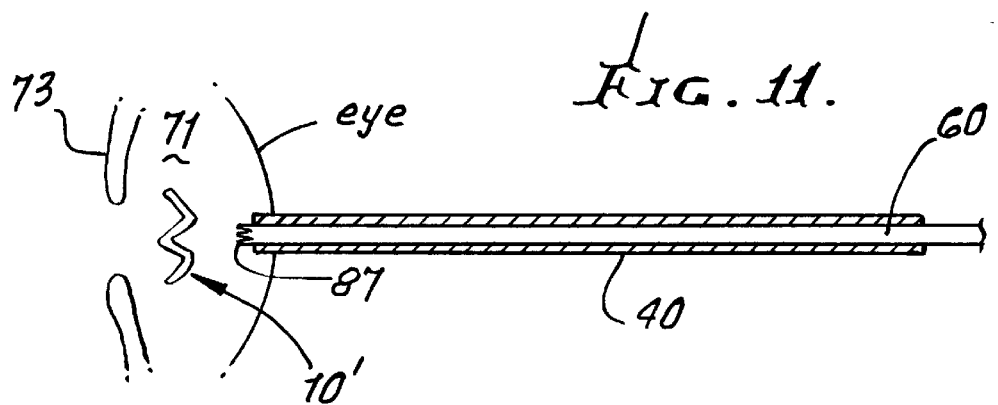

INSERTION OF MULTIPLE FOLDED LENS INTO THE EYE

BACKGROUND OF THE INVENTION

This invention relates generally to insertion of an artificial lens unit into the eye; and more particularly to creation of a multi-folded lens unit, and grasping of same, for insertion into a very small wound opening in the eye, whereby very rapid lens replacement surgery can be achieved, with minimum disruption of the eye.

There is constant need for improvements in eye surgery, particularly in lens implant surgery, to achieve faster and more efficient lens insertion and positioning, as well as reduced size eye wound openings in the interests of faster healing. There is particular need in these regards, for implants in intraocular lens implant surgery.

Prior techniques are believed not to incorporate or suggest the unusual improvements in method and apparatus, which are the subject of the present invention.

SUMMARY OF THE INVENTION

It is a major object of the invention to provide method and apparatus meeting the above needs, and providing for faster, more efficient, and less disruptive lens implant surgery.

Basically, the present method of implanting an artificial lens in the eye includes the steps:

a) providing the lens to have folded M configuration, with two laterally spaced legs interconnected by a U-shaped portion, b) providing an elongated insertion tube having a distal end insertible into the eye, c) traveling the M-folded lens in the tube toward the distal end preparatory to insertion into the eye.

Another object includes expelling the M-folded lens from the distal end of the tube into the eye zone between the corner and iris of the eye, and allowing the lens to at least partially unfold in the zone.

A further object includes manipulating the lens to extend in the intraocular eye zone between the iris and the natural lens of the eye. Such manipulating typically includes i) first deflecting a first edge portion of the lens into the eye zone between the iris and the natural lens, and ii) subsequently deflecting a second edge portion of the lens into the eye zone between the iris and the natural lens.

In this regard, haptics defined by the lens structure may be allowed to become anchored to eye tissue.

Yet another object includes providing an elongated forceps having blades gripping opposite ends of the M-folded lens, the traveling being effected by displacement of the forceps in the tube.

The tube may be squeezed near its distal end to enable sideward release of the blades from the M-folded lens, and withdrawing the forceps endwise in the tube, away from the M-folded lens.

A yet further object includes providing a piston extending in the tube, after withdrawal of the forceps from the tube, and manipulating the piston to expel the M-folded lens from the distal end of the tube, and into an eye zone. As will be seen, the piston typically defines slots located at the end of the piston nearest the M-folded lens, and causing the slots to receive folds defined by the lens, to allow said manipulation.

These and other objects and advantages of the invention, as well as the details of an illustrative embodiment, will be more fully understood from the following specification and drawings, in which:

DRAWING DESCRIPTION

FIG. 1 is a plan view of an artificial lens;

FIG. 1a is an enlarged view of the FIG. 1 looking at it edgewise, with the lens folded into compact M-shape and retained by forceps;

FIG. 1b is a plan view of another form of lens;

FIGS. 2–4 show progressive advancement of the FIG. 1a folded lens by a forceps in a tube adapted for use in implanting the folded lens in the eye;

FIG. 5 is a view like FIG. 4 but showing advancement of a piston in the tube toward the lens, which is now partially unfolded in the tube;

FIG. 6 is a view like FIG. 5 but showing reception of lens edge portions into slots forward at the first end;

FIG. 7 is an enlarged section taken on lines 7—7 of FIG. 6;

FIG. 8 is a view like FIG. 7 but showing different multiple slots in the piston end;

FIG. 9 is an enlarged section taken through the tube and lens, as seen in FIG. 3, and showing squeeze force application to the tube;

FIG. 10 is a view like FIG. 9 but showing squeeze force deformation of the tube into oval shape, to allow forceps release of the lens and retraction;

FIG. 11 is a view showing projection of the tube of FIG. 6 into the eye, and expelling of the lens into the eye by advancement of the piston;

DETAILED DESCRIPTION

Figure 12:
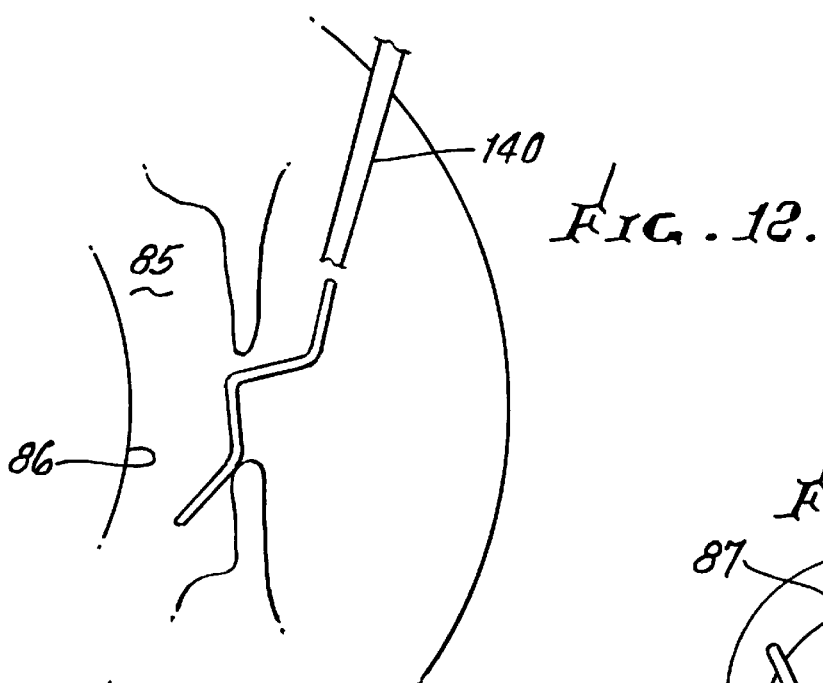
FIG. 12 shows the lens unfolding in the eye.
Figure 13:
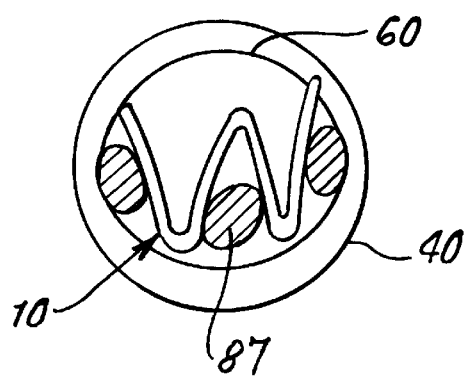
FIGS. 13–16 show various interfits of a slotted piston head with segments of an M-folded lens.
Figure 15:
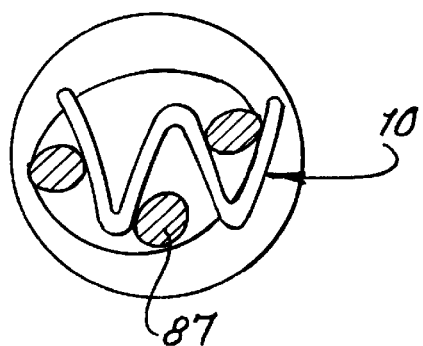
Figure 14:
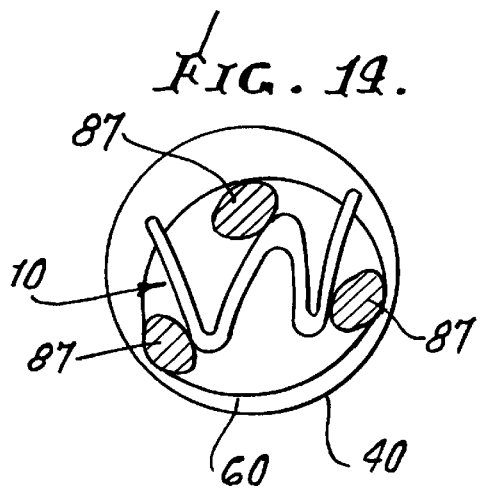
Figure 16:
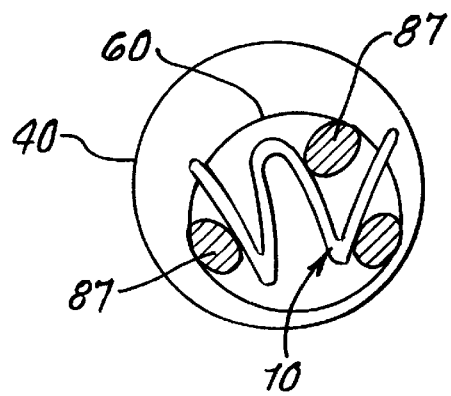

Referring first to FIG. 1, an artificial lens 10 is generally circular and has filament haptics 11 and 12. It may take the form as shown in any of my U.S. Pat. Nos. 5,203,790 and 5,578,080, for example, and the disclosures of which are incorporated herein by reference. FIG. 1b shows an alternate lens 100 having tabular haptics 101 and 102.

In the present case, however, the lens typically consists of a material, such as collamer and silicone resin, characterized by capability for extreme folding, i.e., at three generally parallel locations indicated by lines 13'–15', to produce an M-folded lens 10', as seen in FIG. 1a. Elements, as shown in FIG. 1a, include:

15a middle fold 15b second fold 15c third fold 16a segment of lens U-shaped portion extending upwardly from 15a 16b segment of lens U-shaped portion extending upwardly from 15a and located adjacent 16a 17a leg (or segment) of lens extending downwardly from 15b and located adjacent segment 16a 17b leg (or segment) of lens extending downwardly from 15c and located adjacent segment 16b Also shown in FIG. 1a, in cross-section, are bar or blade elements 30 and 31, such as tongs, of an inserter 19, grasping the lens on legs 17a and 17b. The blade surfaces engaging or pinching the legs preferably bulge toward the legs to compress the lens as shown, whereby the fold portions 15a, 15b and 15c flare outwardly, as indicated. The folded lens occupies minimum width "w" and minimum height "h", for entry into the eye interior via a minimum size incision 140 in the eye, seen in FIG. 12. That wound may, for example, have a slot length of about 0.5 to 2.0 mm, or larger. The smallness of the wound results in minimum disruption of the eye, and promotes faster healing; and the triple folded lens promotes the ability to insert the lens into the eye via such a small wound, in the manner to be discussed.

FIG. 2 shows the M-folded lens 10' being advanced endwise axially in a longitudinally elongated inserter tube 40, which may consist of thin-walled, plastic material and be transparent. The tube has an axis 40a. It may typically be cylindrical at 40c, and tapering at 40b. Such taper may be employed to guide the folded lens and the lens-grasping inserter blades 30 and 31 into the narrowed diameter cylindrical tube extent 40c, easing entry of the lens and blades into and along 40c. The inserter may have elongated arms 44 and 45 to be manually grasped, and connecting segments 46 and 47, as shown, whereby arms may be laterally deflected toward one another to hold the blades in position, as seen in FIG. 1a.

In FIG. 3, the M-folded lens 10' and pinching blades have been advanced toward the distal end 40d of the inserter tube 40; and FIGS. 9 ad 10 show the manner in which the tube may be deformed at the advanced locus of the folded lens, to allow blade retraction in the tube relative to the captivated lens. Note application of finger 48 and thumb 49 pressure to the tube, as indicated by arrows 48a and 49a. This pressure causes tube opposite local walls 40e and 40f to deflect toward one another to grasp the lens at fold regions 15a–15c, as shown, clearance at 51 and 52 being taken up.

The local walls 40g and 40h of the tube are correspondingly expanded apart as shown in FIG. 10, whereby the lens local walls 40e–h form an oval. The clearances at 53 and 54 are enlarged, allowing manipulation of the forceps to separate the blades 30 and 31 away from the sides of the folded lens, and subsequent easy retraction axially of the blades and forceps relative to the folded lens, as seen in FIG. 4. Release of finger pressure to the tube allows the lens to partially unfold and to engage the tube bore 40g, in preparation for lens subsequent advancement and expulsion from the tube into the eye. The forceps is removed from the tube.

FIG. 5 shows axially leftward advancement of a piston 60 in the tube 40, toward the lens 10, to engage the M-folded lens and expel it from the distal end of the tube, as seen in FIG. 11, and into the posterior zone 71 of the eye 70. Zone 71 is between the cornea 72 and the iris 73, and the lens may at least partially unfold in that zone, as shown. Note in FIG. 7 that the end of the piston has three slots 74–76 formed to extend generally axially, in spaced apart relation, to receive at least one of the lens folds, as for example fold 15a if presented toward the piston to be received. Three or four such slots facilitate ease of interfitting of the slots and M-folded lens. The piston may be maneuvered, if desired, to locate the lens in anterior space 85 below the iris, and toward the natural lens surface 86. See FIG. 12. Piston extensions 87 are formed between the slots.

FIG. 8 shows an alternate piston head 90 having four extensions 91 between which four slots 92–95 are formed. Lens fold 15a is shown occupying the slots 92 and 94, for guided travel or advancement by the piston into the eye.

M-folding technique is disclosed in my co-pending application Ser. No. 08/680,683, incorporated herein by reference.

Manufacture of the lens, as shown in FIG. 12, includes:
i) first deflecting a first edge portion of the lens into said eye zone between the iris and the natural lens, and
ii) subsequently deflecting a second edge portion of the lens into said eye zone between the iris and the natural lens.

Finally, inserted lens haptics are typically allowed to become anchored to eye tissue.

If the lens is tilted sidewise in the tube, the piston extensions may interfit the lens segments in any of the ways shown in FIGS. 13–16.

I claim:

1. The method of implanting an artificial lens in the eye, that includes a) providing the lens to have a M-shaped folded and compressed configuration, with two laterally spaced legs interconnected by a U-shaped medial portion, and compressing said legs against said U-shaped medial portion, and acting to hold the legs against said medial portion leaving no open spaces therebetween, b) providing an elongated insertion tube having a distal end insertible into the eye, c) traveling the M-folded and compressed lens in the tube toward said distal end preparatory to insertion into the eye, and locally compressing the tube to allow separation of said legs, d) providing a piston extending in the tube, the piston defining slots located at the end of the piston nearest the M-folded lens, manipulating the piston to cause said slots to receive folds defined by the lens, and manipulating said piston to expel said M-folded lens from the distal end of the tube, and into the eye.

2. The method of claim 1 including expelling said M-folded lens from said distal end of the tube into the eye zone between the cornea and iris of the eye, and allowing the lens to at least partially unfold in said zone.

3. The method of claim 1 including providing an elongated forceps having blades gripping opposite ends of said M-folded lens, said traveling being effected by displacement of said forceps in the tube.

4. The method of implanting an artificial lens in the eye, that includes a) providing the lens to have a folded M configuration, with two laterally spaced legs interconnected by a U-shaped portion, b) providing an elongated insertion tube having a distal end insertible into the eye, c) traveling the M-folded lens in the tube toward said distal end preparatory to insertion into the eye, d) providing an elongated forceps having blades gripping opposite ends of said M-folded lens, said traveling being effected by displacement of said forceps in the tube, e) and including squeezing said tube near said distal end thereof to enable sideward release of said blades from said M-folded lens, and withdrawing said forceps endwise in the tube, away from the M-folded lens.

5. The method of claim 4 including manipulating said lens to extend in the intraocular eye zone between the iris and the natural lens of the eye.

6. The method of claim 5 wherein the manipulating of said lens includes i) first deflecting a first edge portion of the lens into said eye zone between the iris and the natural lens, and
ii) subsequently deflecting a second edge portion of the lens into said eye zone between the iris and the natural lens.

7. The method of claim 6 including allowing haptics defined by the lens to become anchored to eye tissue.

8. The method of claim 4 including providing a piston extending in the tube, after withdrawal of the forceps from the tube, and manipulating said piston to expel said M-folded lens from said distal end of the tube, and into an eye zone.

9. The method of claim 8 wherein the piston defines slots located at the end of the piston nearest said M-folded lens, and causing said slots to receive folds defined by the lens, to allow said manipulation.

* * * * *